US008353290B2

(12) United States Patent
Adams

(10) Patent No.: US 8,353,290 B2
(45) Date of Patent: *Jan. 15, 2013

(54) COMPACT CONTINUOUS POSITIVE AIRWAY PRESSURE APPARATUS AND METHOD

(76) Inventor: Phillip M. Adams, Afton, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/080,433

(22) Filed: Apr. 5, 2011

(65) Prior Publication Data

US 2011/0203592 A1 Aug. 25, 2011

Related U.S. Application Data

(63) Continuation of application No. 11/856,568, filed on Sep. 17, 2007, now Pat. No. 8,011,362.

(51) Int. Cl.
*A61M 15/00* (2006.01)
*A61M 16/00* (2006.01)
*A62B 7/00* (2006.01)
*A62B 9/00* (2006.01)
*A62B 18/00* (2006.01)

(52) U.S. Cl. .............. 128/204.18; 128/200.24
(58) Field of Classification Search ............. 128/200.24, 128/204.18, 202.13, 202.27, 206.27
See application file for complete search history.

(56) References Cited

U.S. PATENT DOCUMENTS

| | | | | |
|---|---|---|---|---|
| 3,220,119 A * | 11/1965 | Jepson et al. | ...................... | 34/99 |
| 3,290,794 A * | 12/1966 | Mango | .............................. | 34/99 |
| 4,257,415 A * | 3/1981 | Rubin | ...................... | 128/200.21 |
| 5,535,738 A * | 7/1996 | Estes et al. | ............... | 128/204.23 |
| 5,606,341 A * | 2/1997 | Aguilera | ......................... | 345/87 |
| 5,647,007 A * | 7/1997 | Wooderson et al. | .......... | 381/332 |
| 5,682,878 A * | 11/1997 | Ogden | ...................... | 128/204.23 |
| 5,893,939 A * | 4/1999 | Rakocy et al. | .................. | 55/471 |
| D427,675 S * | 7/2000 | Hansel | ......................... | D24/110 |
| 6,132,182 A * | 10/2000 | Khan et al. | ..................... | 417/354 |
| 6,164,582 A * | 12/2000 | Vara | ............................... | 242/395 |
| 6,256,192 B1 * | 7/2001 | Shannon | .................. | 361/679.06 |
| 6,295,826 B1 * | 10/2001 | Lee | ................... | 62/244 |
| 6,371,112 B1 * | 4/2002 | Bibi | ........................ | 128/204.18 |
| 6,392,876 B1 * | 5/2002 | Ramonowski | ........... | 361/679.32 |
| D464,724 S * | 10/2002 | Lynch et al. | ................. | D24/110 |
| 6,459,575 B1 * | 10/2002 | Esterberg | ................. | 361/679.47 |
| 6,516,802 B2 * | 2/2003 | Hansen et al. | ........... | 128/207.11 |
| 6,520,607 B2 * | 2/2003 | Pfaff | ............................. | 312/204 |
| 6,554,260 B1 * | 4/2003 | Lipscombe et al. | .......... | 261/142 |
| 6,621,691 B2 * | 9/2003 | Howell | ..................... | 361/679.33 |
| D484,970 S * | 1/2004 | Renz et al. | .................... | D24/109 |
| 6,754,081 B2 * | 6/2004 | Rude et al. | ..................... | 361/725 |
| D493,520 S * | 7/2004 | Bertinetti et al. | ............. | D24/110 |
| 6,820,609 B2 * | 11/2004 | Woodall et al. | ........... | 126/299 R |
| D503,796 S * | 4/2005 | Lithgow et al. | .............. | D24/110 |
| 6,895,964 B2 * | 5/2005 | McAuliffe et al. | ....... | 128/205.24 |
| 7,047,968 B2 * | 5/2006 | Kniewasser | ............... | 128/204.18 |
| 7,195,014 B2 * | 3/2007 | Hoffman | ............... | 128/204.18 |
| 7,195,018 B1 * | 3/2007 | Goldstein | ................ | 128/207.18 |
| 8,011,362 B2 * | 9/2011 | Adams | ..................... | 128/200.24 |
| 2004/0103553 A1 * | 6/2004 | Kroll et al. | ........................ | 34/96 |
| 2007/0045152 A1 * | 3/2007 | Kwok et al. | ................... | 206/733 |
| 2010/0236552 A1 * | 9/2010 | Kwok et al. | ............. | 128/204.21 |

* cited by examiner

*Primary Examiner* — Kristen Matter
(74) *Attorney, Agent, or Firm* — Pate Baird, PLLC

(57) ABSTRACT

A compact continuous positive airway pressure apparatus and method provide a flatter profile and more compact thickness, including a larger lateral dimension in order to be accommodated in conventional luggage designed to stow laptop computers having a smaller aspect ratio of thickness to length or thickness to width. Air tubing may be coiled within a case or coiled as about a spool-like configuration in the base unit of the device.

16 Claims, 15 Drawing Sheets

COMPACT CONTINUOUS POSITIVE AIRWAY PRESSURE APPARATUS AND METHOD

RELATED APPLICATIONS

This application is a continuation of U.S. patent application Ser. No. 11/856,568 filed on Sep. 17, 2007 for COMPACT CONTINUOUS POSITIVE AIRWAY PRESSURE APPARATUS AND METHOD, now issued as U.S. Pat. No. 8,011,362.

BACKGROUND

1. The Field of the Invention

The invention pertains to the field of continuous positive airway pressure apparatus and methods and more particularly to portable systems for active adult users during travel.

2. The Background Art

Continuous positive airway pressure (CPAP) therapy is often used to treat obstructive sleep apnea as well as certain other disorders. In a CPAP apparatus and method, pressurized air is delivered through a mask to a patient's airway. Air may be introduced through the nostrils or through a mask that covers the nostrils and mouth. Typically, such systems are set on a night stand or other support beside a bed, and operate from wall current or a battery power source. Typically, a fan in a "generator" blows ambient air to create a pressurized supply having a pressure of from about five to fifteen centimeters of water. The mask or interface portion of the apparatus may be oral, oral-nasal, or simply nasal in its introduction of air.

Typically, such systems are treated as a medical devices and are engineered to be efficient movers of air through the various passages. Accordingly, such devices typically have a very box-like aspect ratio in which the height, width, and the depth (or thickness, width and length), are typically sized to be of the same order of magnitude. Thus, the aspect ratio is approximately one to one to one (1:1:1:). In the prior art, many such systems have aesthetically pleasing lines developed to make the device seem less rectangular or box-like, yet the overall principal dimensions are about the same.

One of the particular difficulties is the unwieldy size and shape of CPAP systems during travel. Accordingly, each requires a large fraction of the space within a person's luggage. Even supposedly compact or portable CPAP units, when ultimately designed, still have sufficient bulk in all three dimensions as to require a packing system that requires either another piece of luggage or a sizeable portion of the space in other large luggage.

What is needed is an apparatus that can meet several criteria for traveling. The apparatus should fit within luggage configured to hold a laptop computer. If a CPAP system were configured to take on more of the aspect ratios of a laptop computer, then it could be carried as part of carry-on luggage, could be opened for inspection, and could be readily evaluated by conventional security mechanisms in airports. Thus, traveling professionals would not be required to carry such large luggage, or an additional piece of luggage, especially checked luggage, specifically to accommodate the CPAP system.

BRIEF SUMMARY OF THE INVENTION

In view of the foregoing, in accordance with the invention as embodied and broadly described herein, a method and apparatus are disclosed in one embodiment of the present invention as including a housing sized and shaped to fit the space requirements and power requirements typical of a lap top computer.

In accordance with certain embodiments of an apparatus and method in accordance with the invention, a CPAP unit may include a housing, sized and shaped to fit in luggage designed to accommodate conventional laptop computers and their supporting peripherals. The system may typically include a drive system for generating a pressurized air stream at a volume and pressure in accordance with the therapy for which CPAP systems are designed. Likewise, an apparatus and method may include a delivery system of fittings, tubing (hose), and masks in order to deliver the pressurized stream of air into the breathing system of a user.

In certain embodiments, an apparatus in accordance with invention may include various electrical and electronic control systems in order to turn the machine on and off, control the air flow rate or motor speed, and the like. Other systems may be incorporated to accommodate the valving of air flows to and from the lungs of a user. That is, any of the valving systems whereby air may be relieved or expelled from a mask or the delivery system, or the like may be incorporated in a system in accordance with the invention.

The power system may rely on wall power, converted DC power from a wall outlet through a DC power supply, a battery, a computer battery, or the like.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
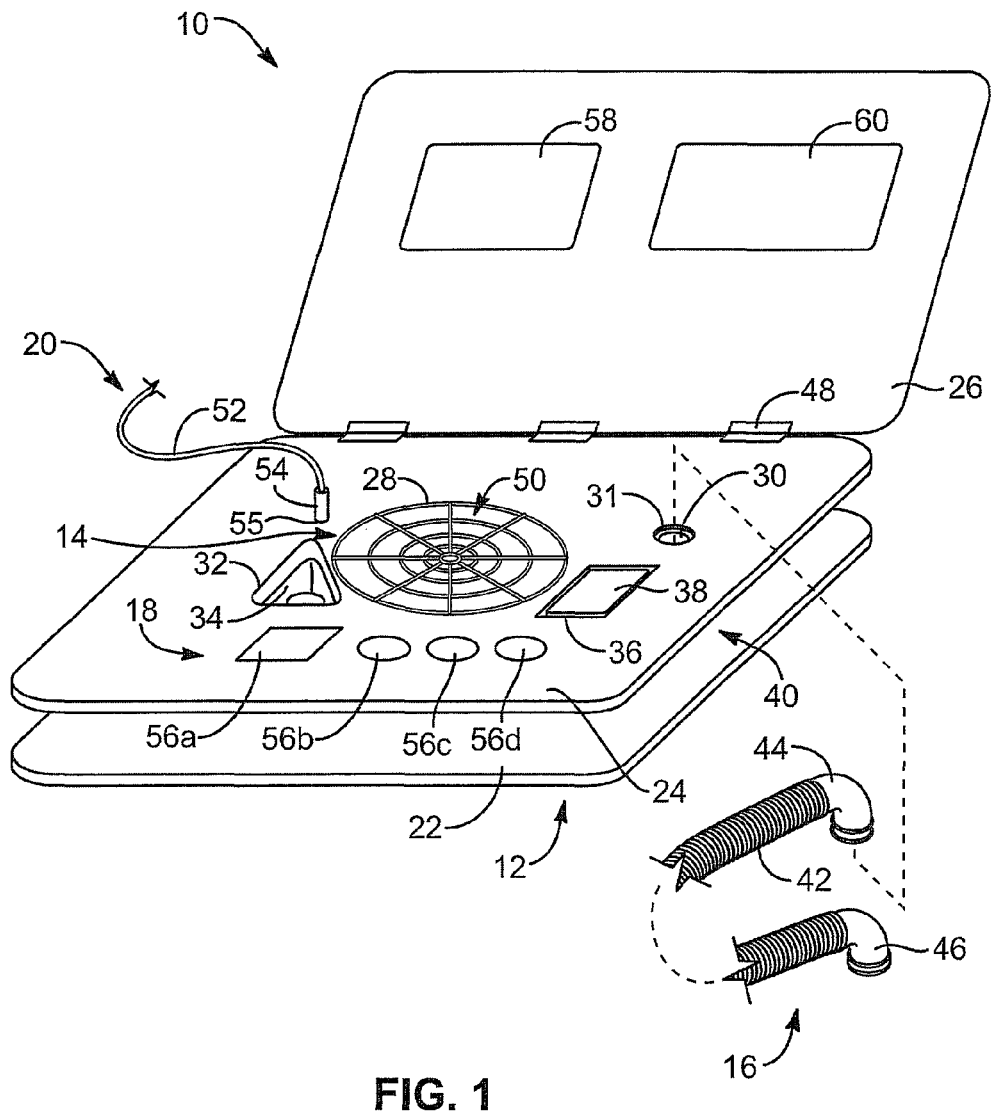
FIG. 1 is a perspective view of one embodiment of an apparatus in accordance with the invention, in which tubing or a delivery hose for the pressurized air supply may be stowed in a spooled configuration within the housing of the apparatus.

Referring to FIG. 1, in one embodiment of an apparatus and method in accordance with the invention, a system 10 or device 10 may be configured to provide a continuous positive airway pressure to a user. In the illustrated embodiment, a housing 12 may contain the basic elements required to drive the air to an elevated pressure. In typical usage, a fraction of a pound per square inch or a fraction of a kilogram per square centimeter will be provided by the system 10, to the airway of a user.

Typically, a drive system 14 provides the prime mover of air. The drive system 14 may draw air from the environment, through a filter, or without a filter, and pressurize it sufficiently to maintain a positive pressure against which a user breathes during sleep. From the drive system 14, a delivery system 16 provides passageways to carry the air to an interface for delivery into the nostrils or mouth of a user, or both.

Typically, a control system 18 may be designed to be as simple or sophisticated as desired for the appropriate therapy. At a rudimentary level the system may be turned off and on. In a more sophisticated embodiment, a selection of the pressure, the net air flow, the profile of the increase of pressure of the air flow, or the like may be controlled in order to provide for the comfort and therapy of a user.

A power system 20 provides a power source to drive the drive system 14. In certain embodiments, a pneumatic power system may be provided. A convenient power system may rely on either wall current or battery power instead. To provide completely self-contained power, a power system 20 may be as simple as a rechargeable battery built into the system 10. Alternatively, a power supply that connects to a wall outlet may service the system equally well. In yet another alternative embodiment, both may be provided in order that a system may be recharged when the wall current is available, but may still be used when wall current is not available.

Referring to FIG. 1, the system 10 may include a base 22 to which to mount the other components of the system 10. A console 23 may be provided in order to accommodate controls, user interface, and other access to the system during operation. The console 24 or console layer 24 may be positioned opposite the base 22, each effectively forming a flange of a spool. Thus, the base 22 and console 24 may actually act as flanges of a spool to receive therebetween the delivery system 16.

In certain embodiments, whether for protection, or simply for purposes of convenience, securement, or closing a display of information or the like, a cover 26 may be provided to close the console layer 24.

In certain embodiments the drive system 14 may be protected by a grid 28 in order to prevent entry of fingers or other small objects into the drive system 14.

Downstream from the drive system 14 an aperture 30 may be provided to discharge air from the drive system into the delivery system 16. A fitting 31 may be provided about the aperture 30 in order to accommodate connection and disconnection of the delivery system 16.

In certain embodiments, storage space 32 may be provided for a mask 34 or interface 34. The storage space 32 may be formed as a recess in the console 24 of the apparatus. In other embodiments the recess 32 may be dispensed with in order to simply store the mask elsewhere. Soft masks may be folded up or otherwise placed in a small space. In certain embodiments, it is desired that the mask 34 be of a substantially stiffer quality, in order to assure a firm seal against the face. Thus, a mask 34 may need storage space 32 within the apparatus 10.

A storage space 36 for a power supply 38 may be provided in the console 24 as well. In the illustrated embodiment, a simple DC power supply 38 may provide the conversion of wall power (alternating current) to be converted to direct current to drive the drive system 14.

A recess 40 or space 40 may be provided between the base 22 and console 24 in order to wrap a hose 42 or tube there around. The hose 42 may be formed in any suitable manner. A convoluted hose may actually provide a very flexible, light, and still comparatively compact system for delivering air from the apparatus 10 to a user. In particular, the hose 42 will connect to the fitting 31 of the aperture 30 to receive air driven by the fan 50.

The fan 50 may be protected by the grid 28 at the inlet where air is received. Accordingly, the fan 50 may blow air to a higher pressure and discharge it through the aperture 30 into the hose 42 for delivery to a mask 34 and ultimately to a user.

In certain embodiments, a cord 52 may deliver power from a power supply or wall current into a plug 54. The plug 54 may fit into a jack 55 formed within the base 22, console 24, or other part of the housing 12 in order to access the drive system 14 and power it. In embodiments where an internal battery is powering the apparatus 10, the cord 52 and plug 54 may simply operate to power the battery during recharging.

In certain embodiments, various buttons 56 or switches 56 may be provided for the system 10. In the illustrated embodiment, various buttons 56a, 56b, 56c, 56d are shown. For example, a button 56a may be a switch to turn the drive system 14 on and off. Other buttons 56c, 56d may control the increase and decrease of the speed of the fan 50.

Other buttons 56d may control other factors, including the display 60. A display 60 may include instructions, may provide feedback information regarding pressure, fan speed, or the like, and may include interactive selections for controlling the apparatus 10 by the user. In general, information and instructions by way of warning and basic set up may also be included in a label 58 simply printed and adhered to a portion of the apparatus 10.

In the illustrated embodiment, deployment of the apparatus 10 may include unwrapping the delivery system 16 including the hose 42 with its fittings 44, 46 from the apparatus 10, such as from a spooled location between the console layer 24 and the base layer 22 acting as flanges of a spool. Accordingly, the fitting 44 may be connected to the output fitting 31, and the fitting 46 to the mask 34. A mask 34 may be formed in any suitable manner, typically of a flexible material in contact with the skin in order to form a good seal, with straps or other secure mechanisms to secure it to the face of a user. The mask 34 may cover only the nostrils, the nostrils and the mouth, or only the mouth. Accordingly, the drive system 14, and the fan 50 in particular, provides pressurized air through the aperture 30 into the tubing 42 for delivery into the mask 34 at an increased pressure above ambient pressure.

Meanwhile, the power supply 38 may be removed from its storage location 36 and plugged into outlet power in order feed the cord 52 and the plug 54 connected to power the motor driving the fan 50.

Upon waking, a user may stow the system 10 by removing the fitting 44 from the aperture 30 with its retaining fitting 31 and removing the mask 34, optionally, from the mask fitting 46. In some embodiments, a more compact system may have a foldable or very flexible mask 34. The mask fitting 46 may also be formed integrally between the tubing 42 and the mask 34 making removal of the mask 34 from the tubing 42 unnecessary. Likewise, the fitting 31, 44 need not be readily separable, nor separable at all, nor distinct from one another.

In either mode, the tubing 42, whether or not removed from the fitting 31 or mask 34 may be spooled around the space 40 between the base 22 and console 24 to stow it. Detents may be provided by way of bosses, tabs, or simply a closer proximity to one another of the edges of the base 22 and console 24 in order to retain the tubing 42 therebetween. After final stowage of the power supply 38 in its storage location 36, the lid 26 or cover 26 may be closed on hinges 48 against the console 24 in order to close the system up for travel.

Figure 2:
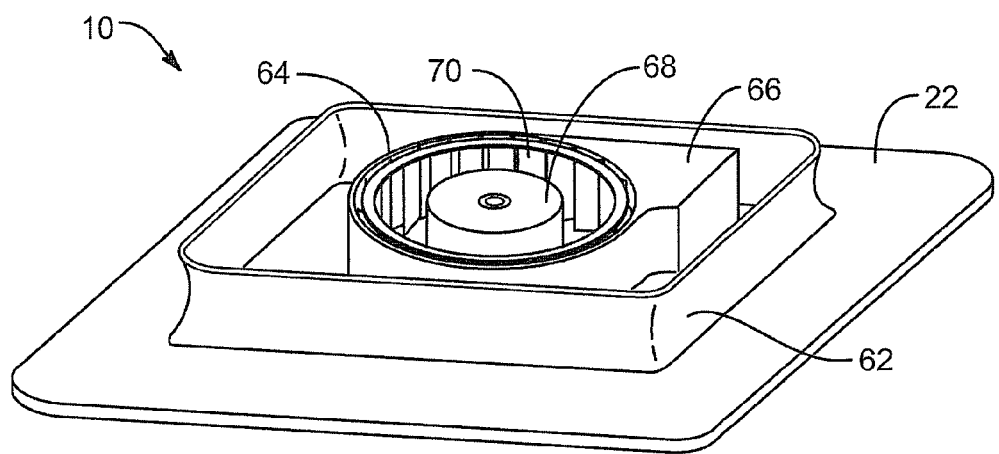
FIG. 2 is a perspective view of one embodiment of the spool center and the fan system of the apparatus of figure one, having the lid and upper console portions removed.

Referring to FIG. 2, a view of the apparatus 10 of FIG. 1 is illustrated showing only the base 22 with selected components located below the console 24. In the illustration, a spool portion 62 or mandrel 62 for receiving the tubing 42 may be located between the base 22 and the console 24. Within the periphery of this spool portion 62, or mandrel 62, the fan 50 may operate.

In the illustrated embodiment, the fan 70 represents a generic fan 50 of FIG. 1. In the illustrated embodiment, the fan 70 is a squirrel-cage type fan and the motor 68 is embedded within the confines of the fan 70. A shroud 64 surrounds the fan 70 to direct the air to an output duct 66.

The spinning of the fan 70 about the motor 68 (by the motor 68) causes the air to move radially away from the fan 70, while also moving the air circumferentially with respect to the outer circumference of the fan 70. Accordingly, the duct 66 is filled with pressurized air, while the region within the circumference of the fan 70 is decreasing in pressure as it draws air through the grid 28 and through the fan 70.

Figure 3:
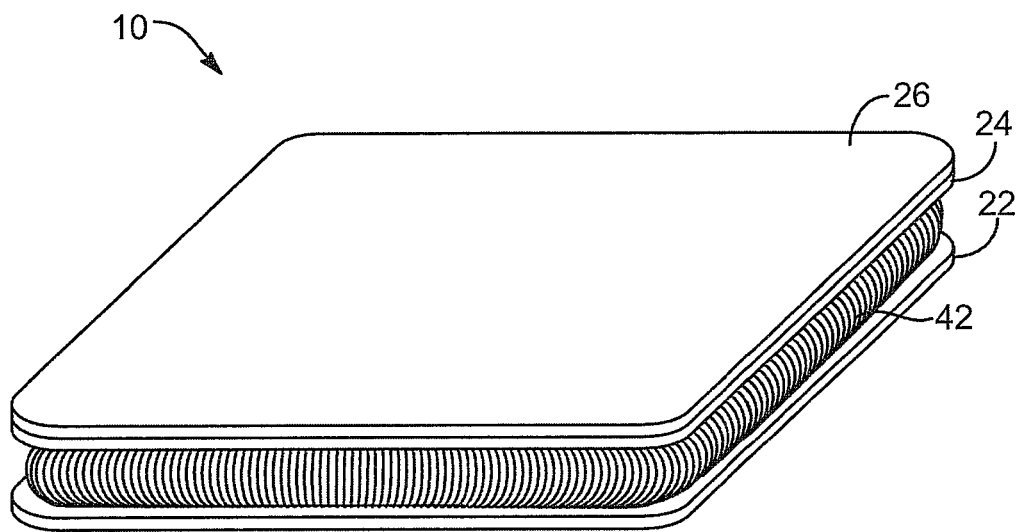
FIG. 3 is a perspective view of one embodiment of the apparatus of FIG. 1 in a closed configuration with the tubing stowed therein.

Referring to FIG. 3, the apparatus 10 in the illustrated embodiment may fold up with the cover 26 against the console 24, forming a compact package between the base 22 and the cover 26. Meanwhile, the hose 42 or tubing 42 is spooled around the mandrel 62 in order to fit within the overall envelope defined by the juxtaposed base 22 and cover 26.

Figure 4:
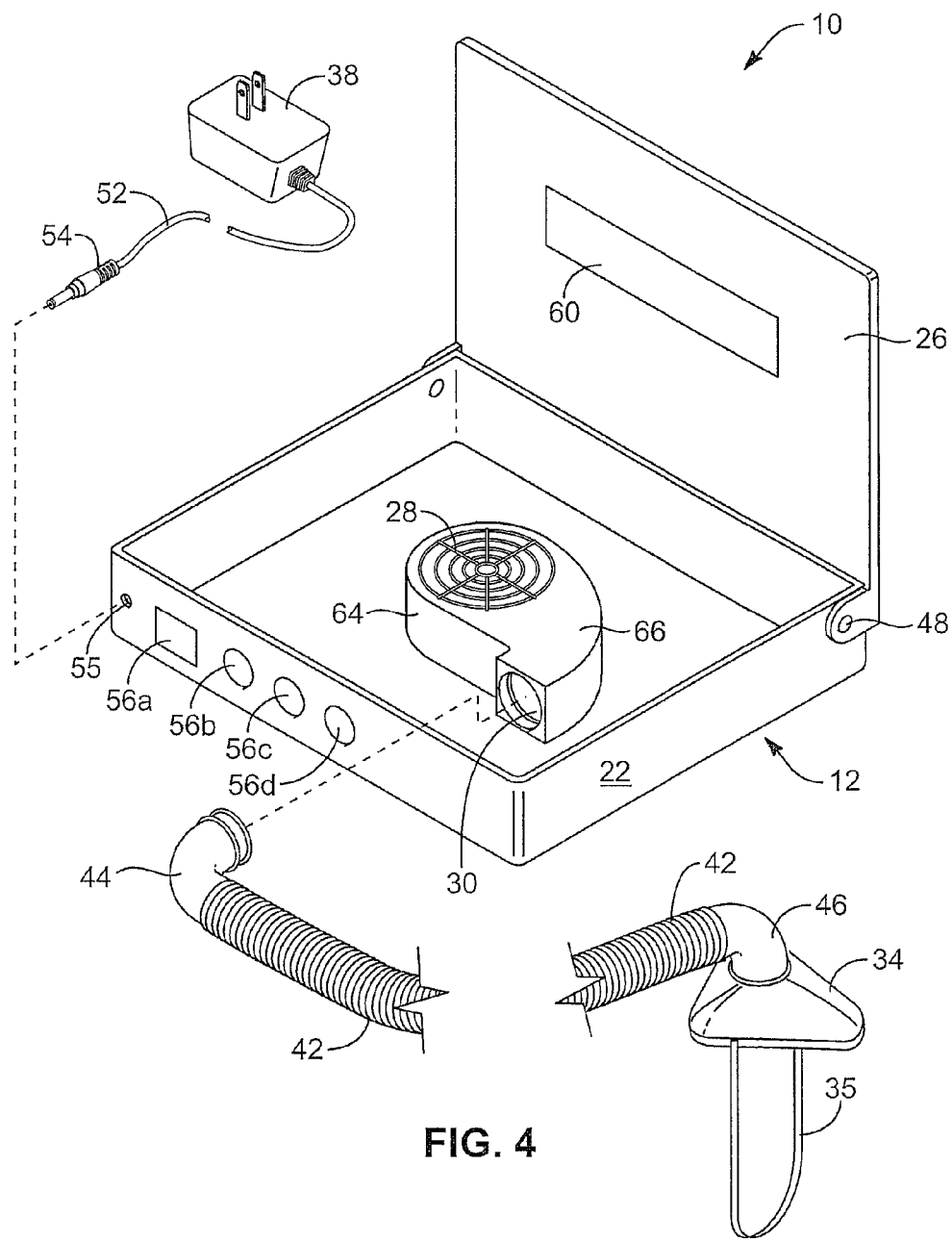
FIG. 4 is perspective view of an alternative embodiment of an apparatus in which a cavity is available to stow the tubing and mask completely within an outer case, to be not visible when the case is closed.

Referring to FIG. 4, an apparatus 10 may have a housing 12 formed of a base 22 and a cover 26. The base 22 and cover 26 may be connected by a hinge 48 pivotable between a closed and an open position. In FIG. 4, the apparatus 10 is shown in an open position with the tubing 42 removed from stowage along with the power supply 38 for use. In the illustrated embodiment, the delivery system 16 is constituted by the tubing 42 with its associated fittings 44, 46 and mask 34, having a strap 35 for securement to the face of a user.

Meanwhile, the drive system 14 is enclosed within a shroud 64 and the fan 50 is behind the grid 28 provided for protection. The aperture 30 is connectable to the fitting 44 to direct pressurized air from the duct 66 provided as an outlet from the shroud 64 delivering pressurized air from the fan 50 into the tubing 42. In the illustrated embodiment, the control buttons 56 may be provided on the case 12 or housing 12 in any suitable location. In the illustration, the control buttons 56 are positioned on the base 22. Likewise, the jack 55 for receiving the plug 54 from the power supply 38 and cord 52 is located on the front face of the base 22.

Accordingly, the power can be converted from wall power to DC current by the power supply 38 and delivered through the plug 54 and jack 55 to the motor 50 inside the shroud 64. Controls 56 may be used for controlling on, off, pressure, power, speed, or the like. The display 60 may provide instructions for monitoring of the operation of the apparatus 10.

Figure 5:
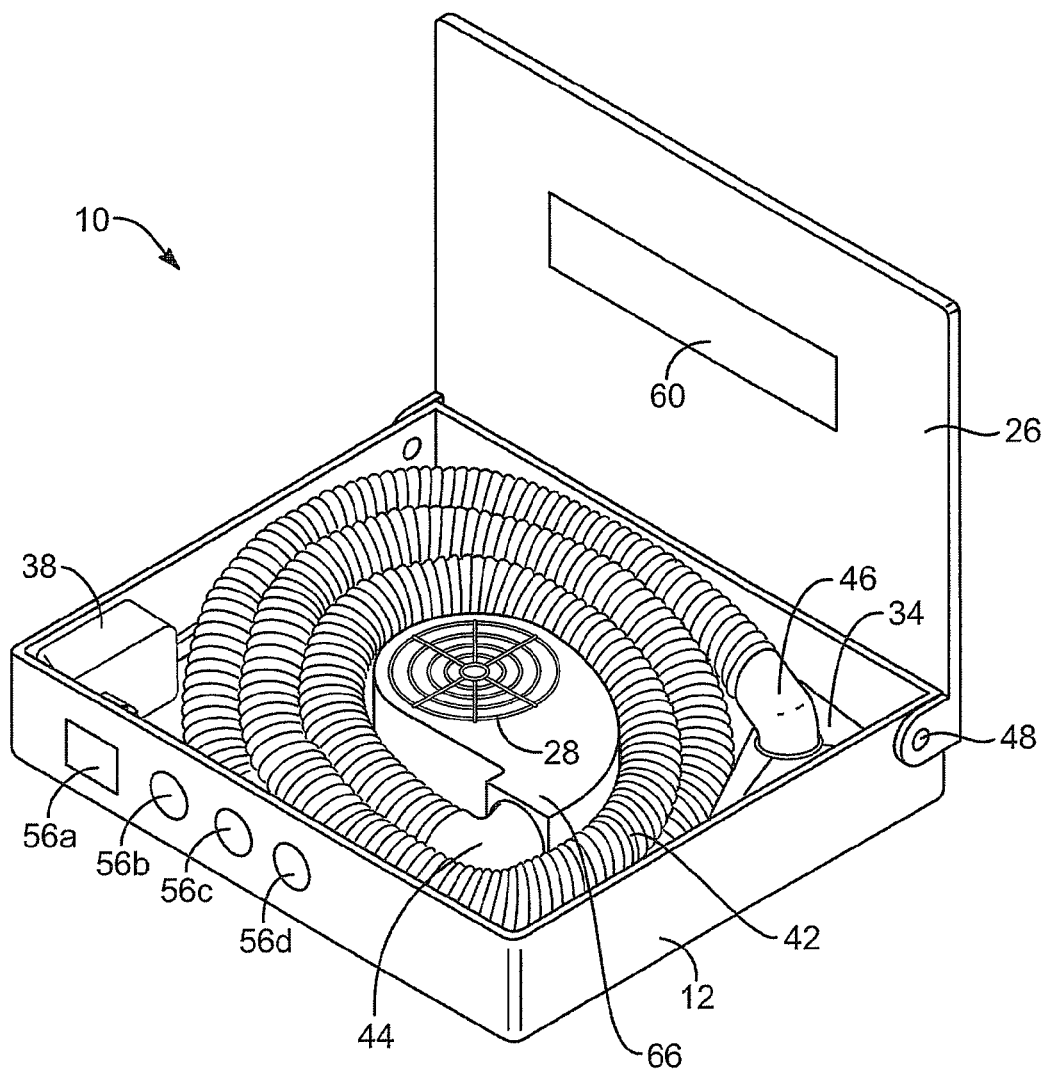
FIG. 5 is a perspective view of the apparatus of FIG. 4 illustrating the stowed mask and tubing with associated fittings.

Referring to FIG. 5, the apparatus 10 of FIG. 4 may be placed in a stowed configuration by wrapping the tubing 42 about the drive system 14 containing the fan 50 and shroud 64. The fitting 44 may be disconnected from the aperture 30 or remain in it. Likewise, the fitting 46 may be removed from the mask 34 or remain connected. The mask 34 in the illustrated embodiment may be stowed within the base 22 just as the tubing 42 or hose 42. Thus, closure of the lid 26 or cover 26 against the base 12 provides an envelope that is approximately that of a laptop computer and encloses the accompanying supporting peripheral elements of the apparatus 10 in a compact and easily transportable unit. Various types of sealing mechanisms such as bosses, knobs, ridges or other detents within the hinge 48, or between the cover 26 and base 22 may be implemented in accordance with principles or devices known in the art.

Figure 6:
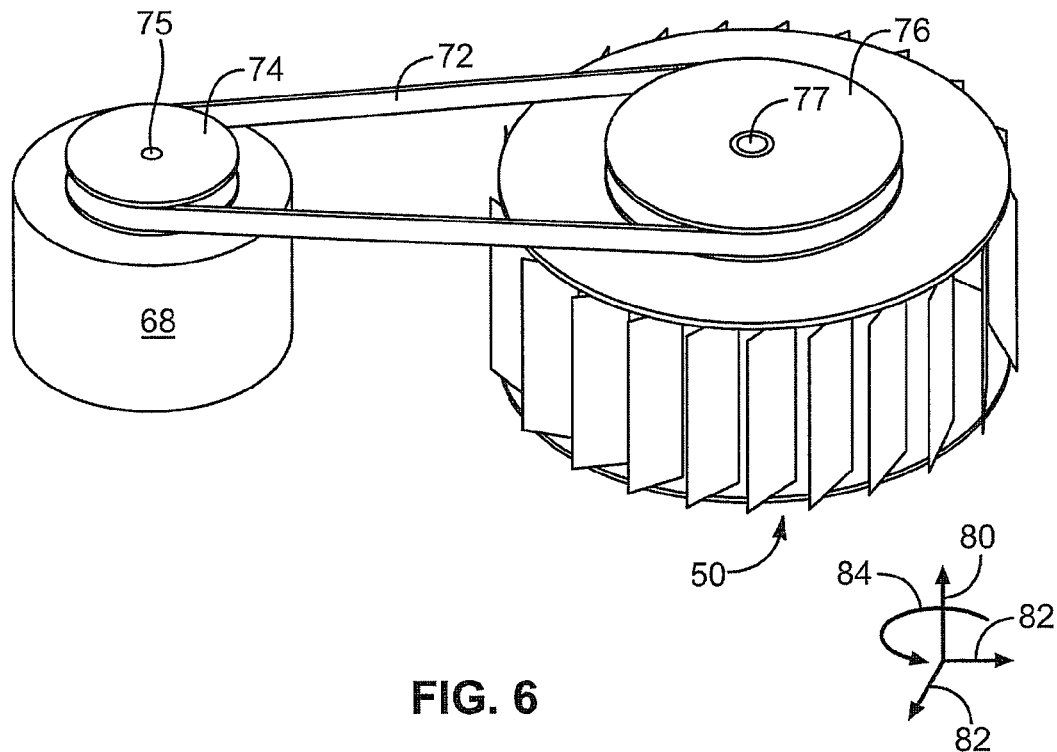
FIG. 6 is a perspective view of one embodiment of a motor and fan system suitable for implementation in an apparatus in accordance with the invention.

Referring to FIG. 6, an apparatus 10 in accordance with the invention may include a fan 50 connected directly to a motor 68, or connected indirectly as illustrated. In the illustrated embodiment of FIG. 6 the motor 68 is connected to the fan 50 by a set of pulleys 74, 76 and corresponding shafts 75, 77. A belt 72 connects the pulleys 74, 76 in order to drive the fan shaft 77 from the motor shaft 75.

In the illustrated embodiment, the axial direction 80 represents the direction of intake, while the radial directions 82 represent the direction that air moves in response the spinning of the fan 50. A shroud 64 around the fan 50 may restrict the flow of air and directly into a particular duct 66 as described hereinabove. In response to the rotation of the fan, the space in the center of the fan 50 is evacuated or rather contains air at reduced pressure, while the area around the circumference of the fan represents air being driven in a radial 82 and a circumferential 84 direction. The shrouding 64 prevents air from escaping the fan 50, while the ducting 66 provides a location or plenum for the air to accumulate at elevated pressure in order to be driven out the aperture 30 to the tubing 42.

Figure 7:
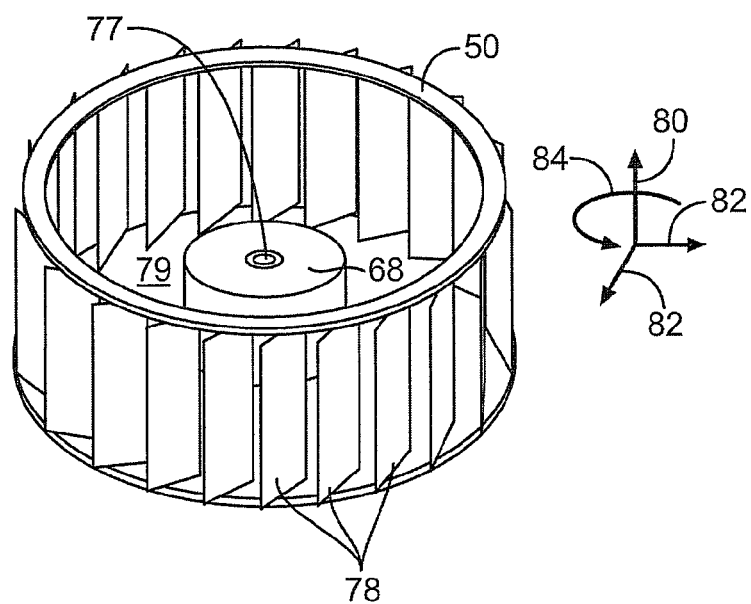
FIG. 7 is perspective view of an alternative embodiment of a fan and motor system suitable for pressurizing air in an apparatus in accordance with the invention.

Referring to FIG. 7, in an alternative embodiment, a motor 68 may be embedded within the fan 50 in order to reduce the overall size of the system 10. However, if the fan 50 is formed to be of a comparatively thin profile, then the motor may need additional space. Meanwhile, the vanes 78 tend to drive the air in a circumferential direction 84, resulting in acceleration in a radial direction 82. As the air escapes from the vanes 78 or blades 78 of the fan 50, it may have both a circumferential 84 and a radial 82 component of velocity. Accordingly, it may be ducted as described hereinabove.

In typical embodiments, the fan 50 may be formed of vanes 78 projecting (for example, at right angles) from a disk 79 or base 79. Typically, the base 79 will include a hub for receiving a shaft 77 on the motor 68. Any suitable attachment mechanism including keys, set-screws, friction, splines, and the like may be used to secure the shaft 77 to the fan 50.

Figure 8:
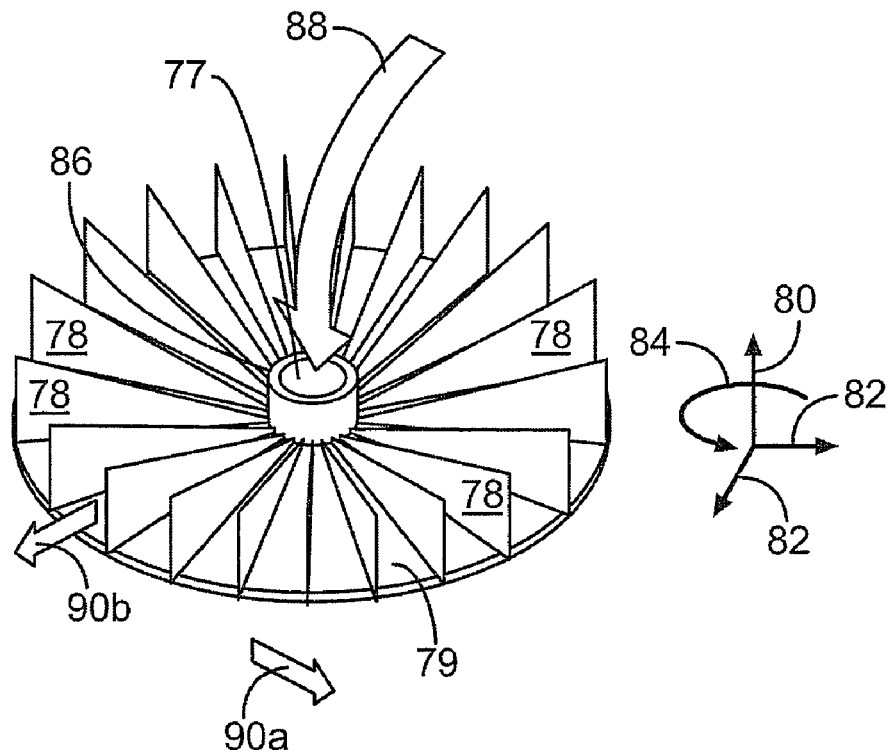
FIG. 8 is a perspective view of an alternative embodiment of a fan suitable for developing a flow of pressurized air in an apparatus in accordance with the invention.

Referring to FIG. 8, in one embodiment of an apparatus 10 in accordance with invention, the fan 50 may actually be configured with vanes that taper toward the center hub 86, having their greatest height from the frame 79 or disk 79 near the outer periphery thereof. Accordingly, the vane 78 may actually act as trapezoidal or triangular vanes that are very short axially with respect to the disk 79 near the hub 86, and very tall near the outer periphery of the disk 79.

Thus, the air flow in 88 will be drawn in an axial direction into the fan while the blades 78 or vanes 78 rotate, the air moves in a circumferential direction 84. A response of the air is to flow outwardly in a radial direction 82 such as the flow illustrated as flow 90b. Ultimately, however, the shroud 64 and duct 66 will permit escape of the air only in a circumferential direction 84 illustrated as the airflow 90a exiting the fan 50.

The squirrel cage fan of 57, and the vane fan of FIG. 8 both tend to be centripetal or centrifugal fans. That is, the pressure comes as a result of the spinning of the air, and its tendency to want to escape radially 82 from the circumferential motion 84. That is, any motion in a circumferential direction 84 is actually an acceleration toward the center shaft 77, and the air preferentially migrates radially 82.

Figure 9:
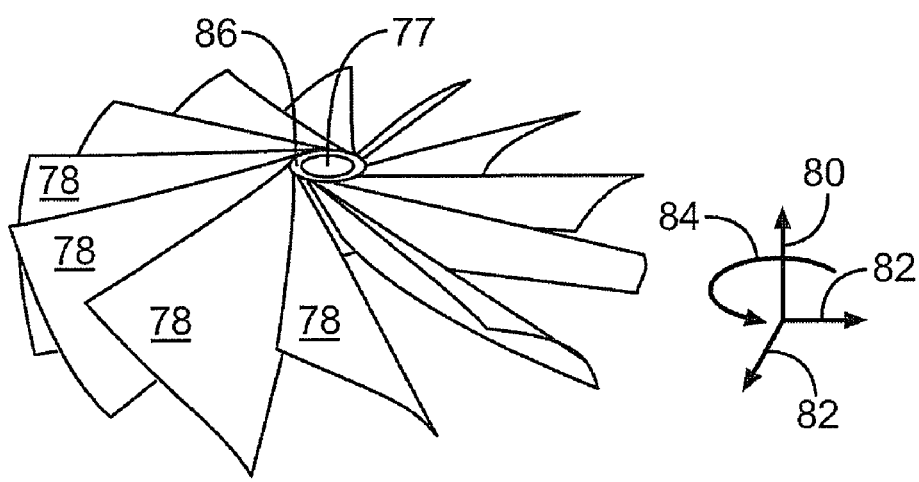
FIG. 9 is a perspective view of an alternative embodiment of a fan, designed to provide an axial flow of pressurized air in an apparatus in accordance with the invention.

Referring to FIG. 9, another embodiment of the fan 50 may include a shaft 77 and hub 86 from which various vanes 78 extend outward. In the embodiment of FIG. 9, air is actually inducted from one side of the fan 50 in an axial direction 80, and is discharged out the other side in the same axial direction 80. Of course, in the illustrated embodiment, the direction of rotation in the circumferential direction 84 determines which direction or sense the air flow will actually take in the axial direction 80.

One of the advantages of a squirrel cage fan 50 or a vane fan 50 is a comparatively thin profile on the order of from about one half inch to about an inch and a half, perhaps up to two inches. On a substantially larger radius of from about one and half to about four inches, the fan may provide a comparatively large flow rate (e.g. 0.1 to about 2 cfm), large pressure increase (e.g. 5 to 30 cm of water), or the like, into a comparatively smaller duct, such as the duct 66, and the tube 42. One benefit of the fan 50 illustrated in FIG. 9 is that a comparatively quite fan with a minimal direction change may be implemented. Many pancake fans 50 may actually include a motor within the hub 86 in the fan 50 of FIG. 9, thus forming a comparatively compact, axial drive system 14.

Figure 10:
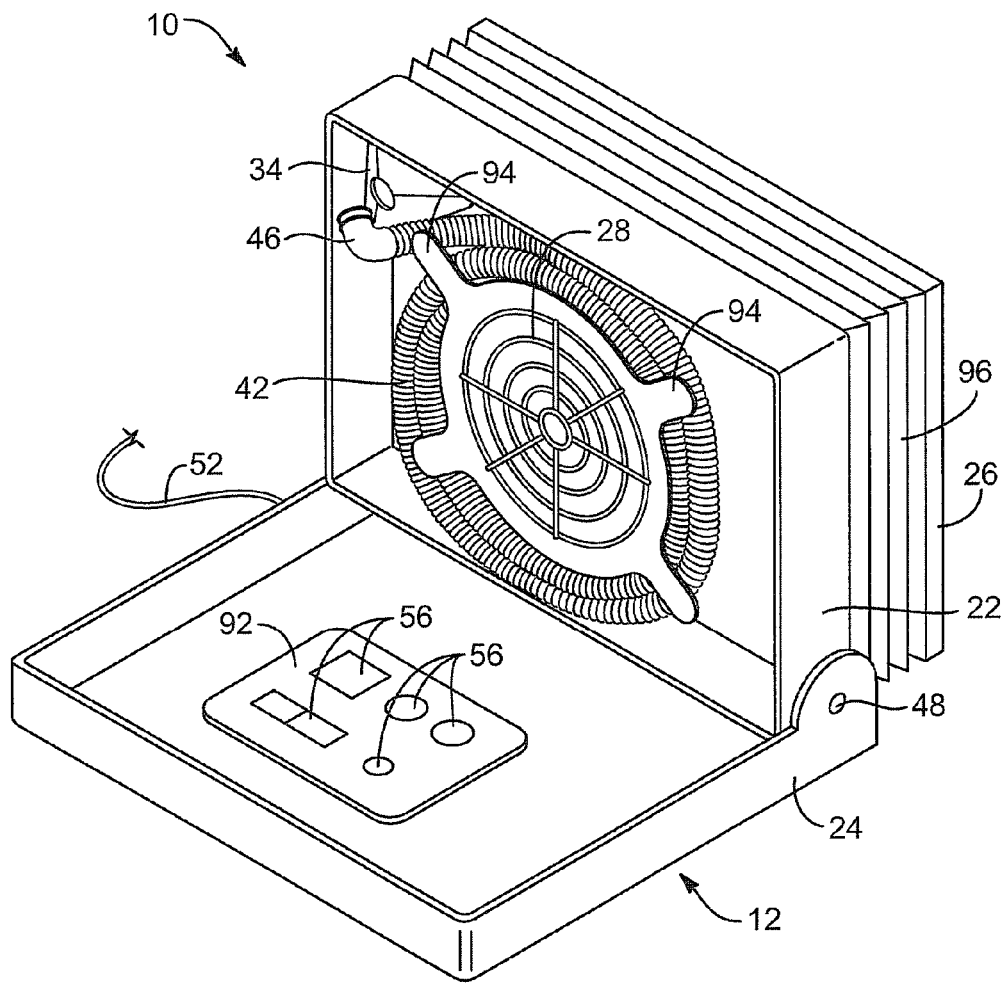
FIG. 10 is a perspective view of an alternative embodiment of an apparatus in accordance with the invention, having a capability to expand a plenum for development of a larger supply of pressurized air.

Referring to FIG. 10, an apparatus 10 may include a housing 12 having a base 22, console 24, and cover 26. Likewise, a drive system 16 may include a fan 50 under a grid 28 to drive airflow into a tube 42. In the illustrated embodiments, the console portion 24 actually becomes the bottom of the housing 12, when stowed. Nevertheless, the control buttons 56 may be provided on a panel 92 associated with the console layer 24 of the apparatus 10. Likewise, some type of power line 52 with its associated plug 54 may provide power into the system by any of the mechanisms discussed above or known in the art. Meanwhile, the mask 34 may be stowed with the tubing 42 and its associated fittings 44, 46 within the space available in the base 22.

Figure 11:
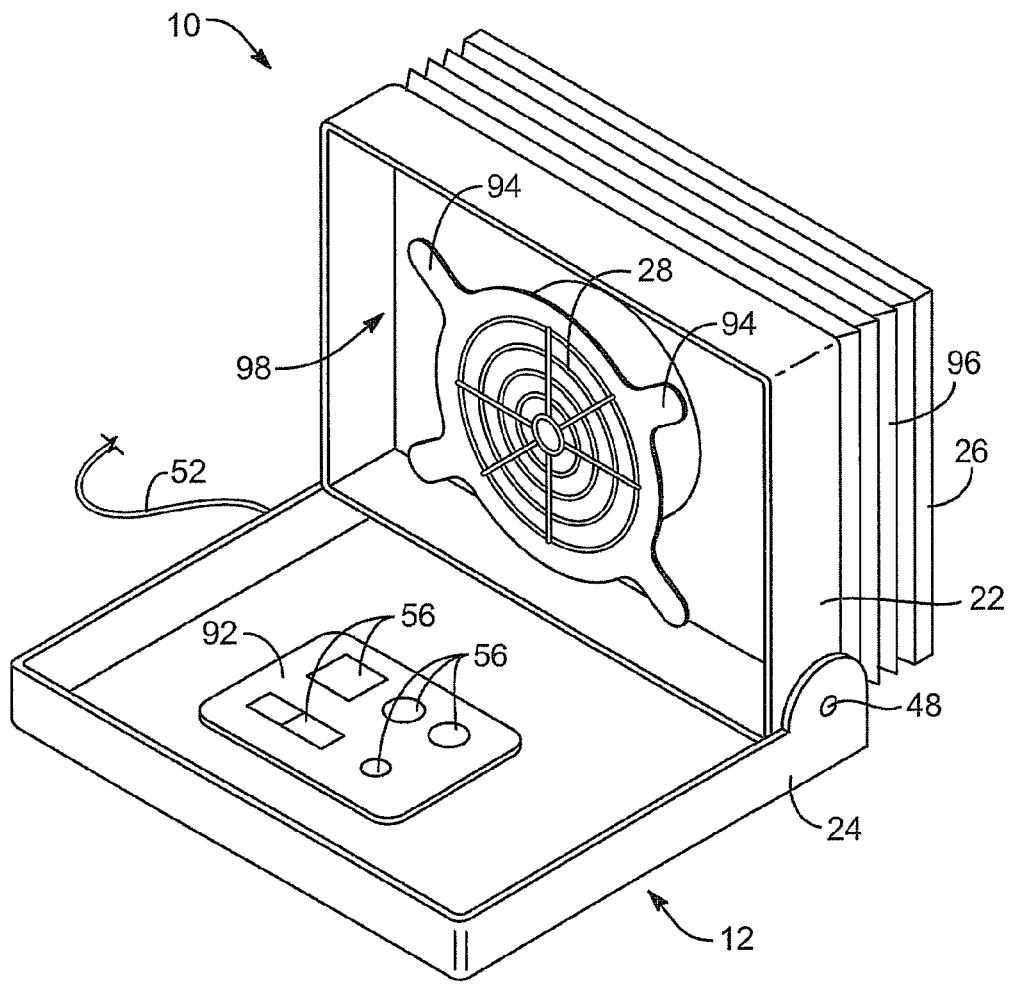
FIG. 11 is a perspective view of the apparatus of FIG. 10 with the tubing removed from the case for deployment.
Figure 12:
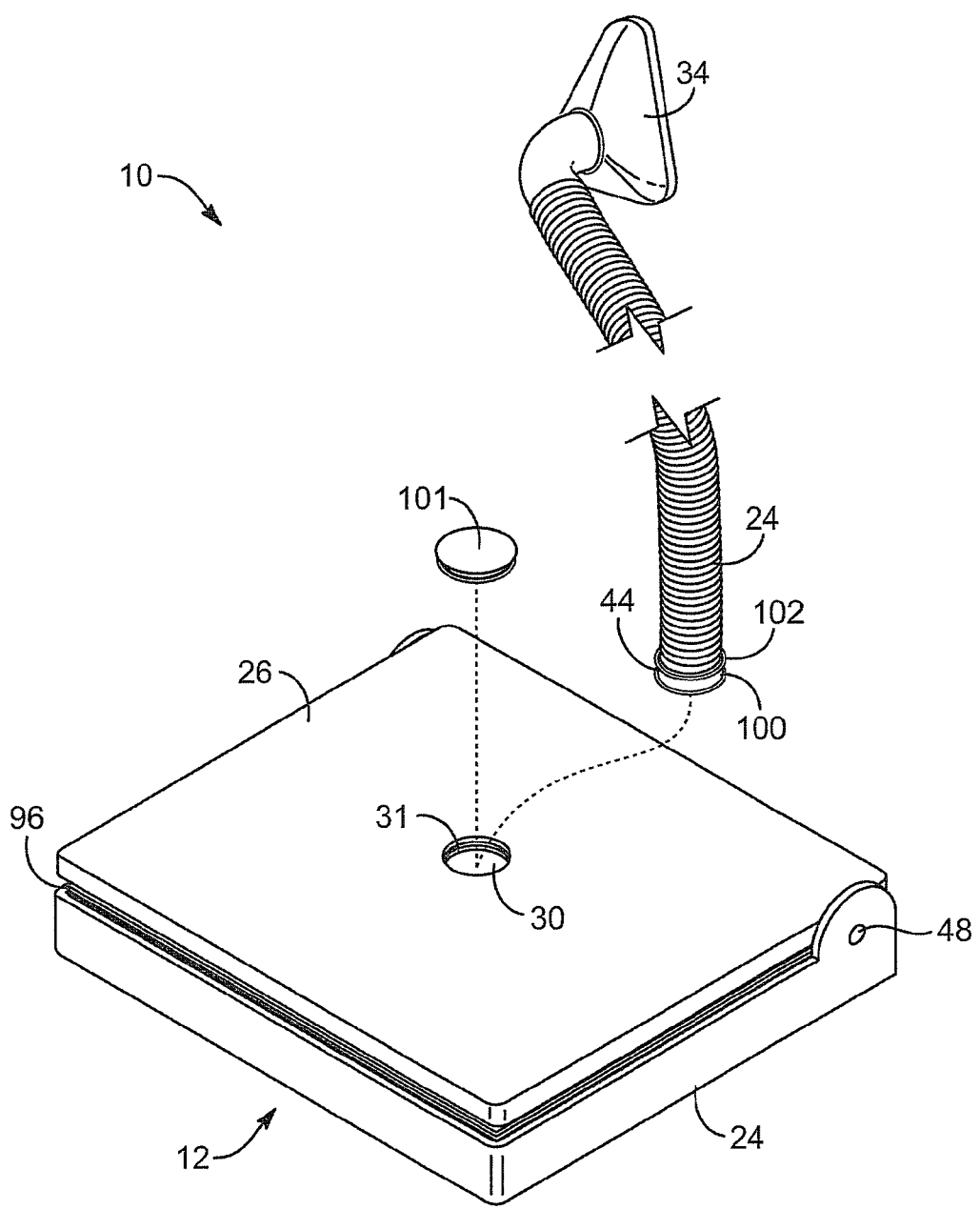
FIG. 12 is a perspective view of the apparatus of FIGS. 10 and 11 illustrating the position of the aperture and connector feeding the tubing and mask of the apparatus from the lid side of the plenum chamber.

In the illustrated embodiment of FIGS. 10-12, retainers 94 may provide flexible or rigid restraints in order to hold the tubing 42 in place during stowage. In one embodiment, the retainers 94 may be formed of a flexible plastic or stiff rubber such that they may be easily deflected in order to place the tubing behind them. The retainers 94 may be replaced by belts, straps, or the like, securing to the base 22 in certain embodiments.

By either means, the tubing 42 may be wrapped for stowage within the base 26. Meanwhile, the grid 28 covering the fan 50 may cover a squirrel cage fan 50, a vane fan 50, an axial fan 50, or any other suitable mechanism. In the illustrated embodiment, an optional bellows 96 is included. The bellows provides an expansion space between the base 22 and the lid 26 in order to provide a plenum or expanse of space or volume in which a volume of air under pressure can be collected.

The value of a plenum is that pressures are moderated somewhat in response to the breathing of an individual, or changes in output. For example, whenever an individual is breathing against the pressure of air within the tubing 42, pressure rises behind the fan 50. This effect may be somewhat ameliorated by providing a plenum that tends to have sufficient volume to absorb the instantaneous fluctuations in pressure and volume of air.

Any suitable support including the bellows alone, or flexible joints, struts, or the like may be used to support the cover 26 with respect to the base 22. In such an embodiment, the system may actually expand to a larger size than its stowed size in order to create a plenum within the bellows 96 and the lid 26.

Referring to FIG. 12, the apparatus of FIGS. 10 and 11 is illustrated in a stowed configuration. For clarity, the hose 42 has been removed from the housing 12 in order to illustrate an embodiment of how the fitting 44 may fit onto the cover 26 in the aperture 30. When the fitting 44 is removed from the aperture 30, and its associated fitting 31, a cap 101 fitted to the fitting 31 may be inserted to prevent damage, dirt, and the like. In the illustrated embodiment, the lid closes against the bellows 96, but may close over the bellows, in order to close up against the console 24, which forms the outer shell of the housing 12. Meanwhile, the base 22 is fit down into the console portion 24.

In general, the hose 42 may be connected in any suitable manner. In the illustrated embodiment, the mask 34 may be secured permanently or temporarily to the hose 42. The fitting 44, typically permanently attached to the hose 42, may include both a securement 100 and a stop 102. The purpose of the securement 100 is as a detent to engage the fitting 31. The purpose of the stop 102 is to prevent the fitting 44 penetrating further into the aperture 30. Any suitable mechanism may be used including threads, quick release couplings, interfering "o" rings, or the like.

In general, the space 98 for storage of the hose 42 may actually be used as a plenum in certain embodiments. That is, for example, the space 98 may be configured on the opposite side of the base 22, between the base 22 and the cover 26 in order to form a plenum after the hose 42 is removed therefrom. Accordingly, the surface defined by the edges of the base 22 closest to the console 24 may be a solid surface except for the opening for the grid 28.

The bellows 96 is not required. Thus, the illustration of FIG. 12 shows the housing 12 in substantially the stowed configuration, but with the cap 101 removed. Meanwhile, the hose 42 is illustrated in order to show its positioning and sealing with respect to the aperture 30.

Figure 13:
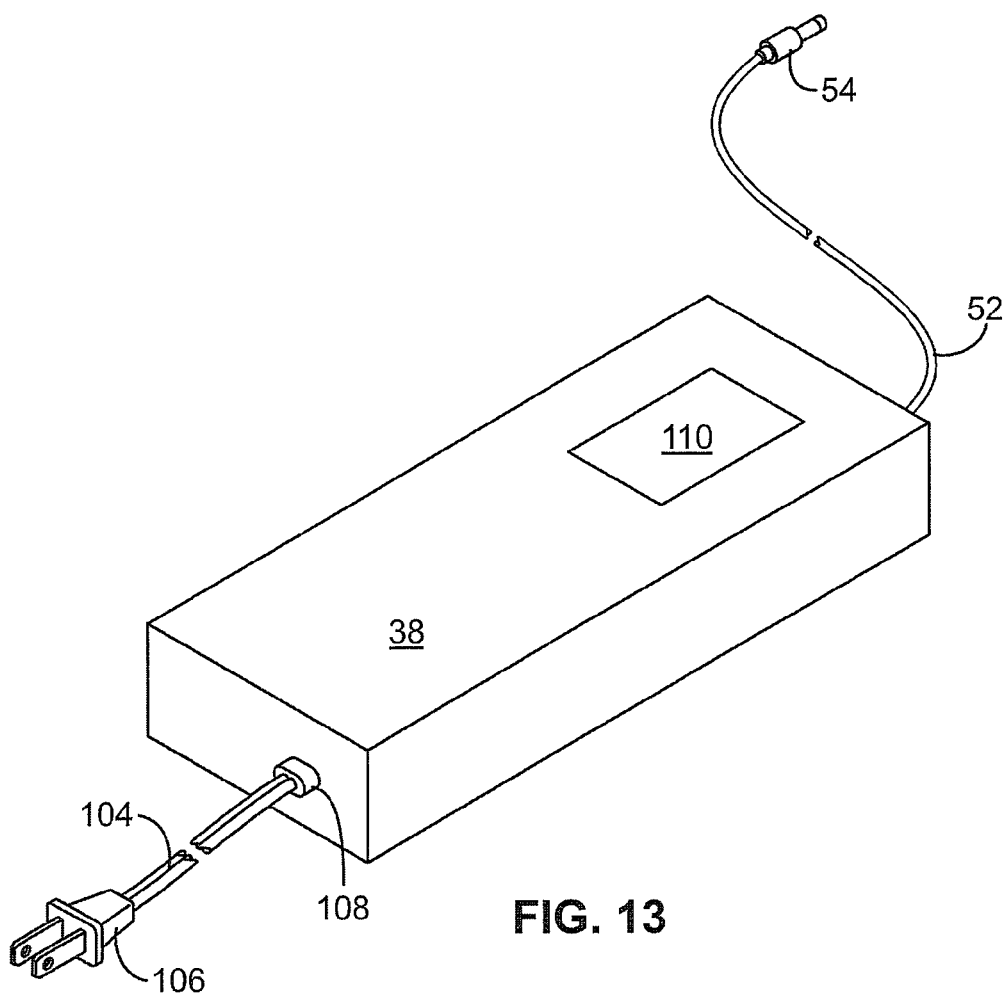
FIG. 13 is a perspective view of one embodiment of a power supply suitable for powering an apparatus in accordance with the invention.

Referring to FIG. 13, the power system 20 for the apparatus 10 in accordance with the invention may be one of several possible configurations. For example, a power supply 38 may include the appropriate hardware to convert alternating current to direct current for convenience, and safety. Thus, a cord 104 may come from wall power through a plug 106 to be connected by the adapter 108 to the power supply 38. Wall current may be converted from alternating current, at a comparatively higher voltage, to direct current, at a comparatively lower voltage, delivered through the cord 52 and subsequently the plug 54 into the apparatus 10. Typically, a plate 110 commonly called a rating plate or "boiler plate" may contain information concerning safety, ratings, instructions, warnings, connection requirements, and the like.

Figure 14:
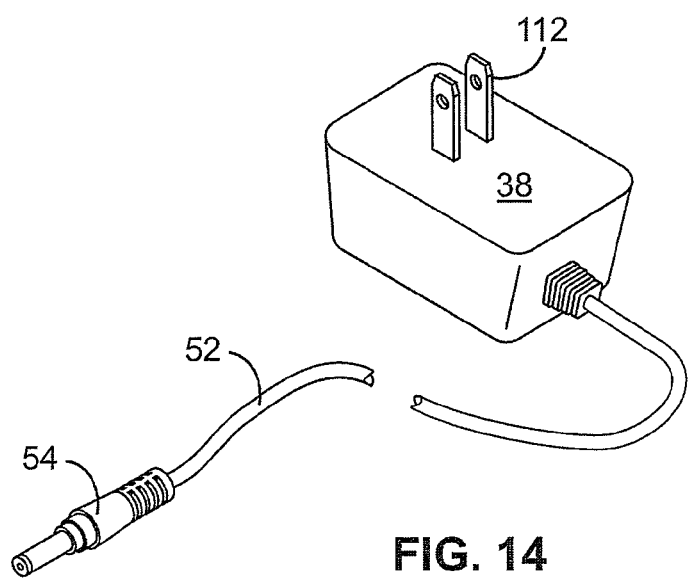
FIG. 14 is a perspective view of an alternative embodiment of a power supply suitable for portability and for powering the apparatus in accordance with the invention.

Referring to FIG. 14, a compact power supply may be used in many situations requiring comparatively lower power (e.g. a few amps or less). The apparatus 10 does not require large amounts of power (e.g. typically less than an amp down to tenths of an amp). A simple adapter 38 or power supply 38 may provide a plug 112 directly into a wall socket, feeding direct current through a cord 52 and a plug 54 into the apparatus 10.

Figure 15:
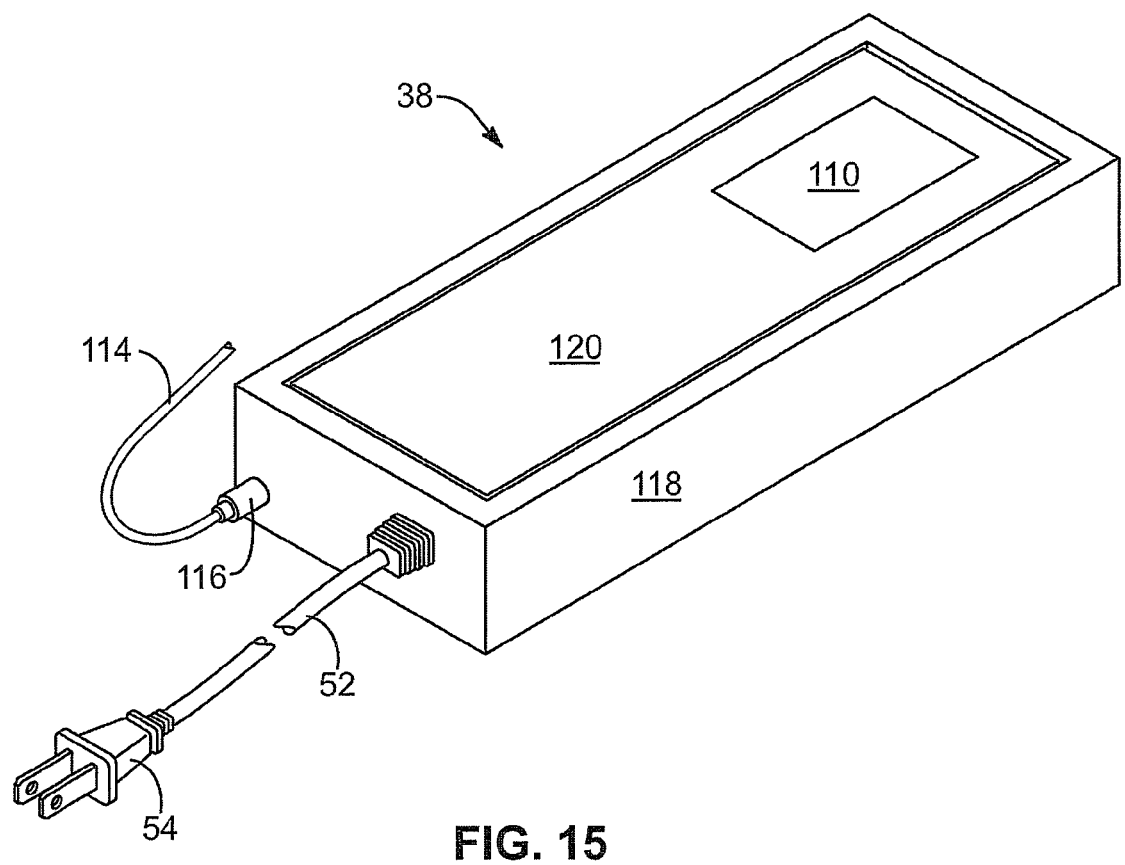
FIG. 15 is a perspective view of one alternative embodiment of a rechargeable battery suitable for use to power an apparatus in accordance with the invention, or suitable for recharging a computer battery for use in both a laptop computer and a CPAP system in accordance with the invention.

Referring to FIG. 15, in one embodiment, an apparatus 10 in accordance with the invention may use a battery 120. The battery 120 may be identical to, or may be the same battery 120 as that of a laptop computer. Accordingly, a charger 118 or cradle 118 may be used to charge the battery 120, or the battery 120 may be charged within a laptop computer.

A CPAP apparatus 10 may be carried with a computer and may share the same battery 120. In the illustrated embodiment, a battery 120 may be fitted into a cradle 118 connected to wall power or a power supply by a cord 114, and secured electrically by a plug 116 in the cradle 118. In the illustrated embodiment, the output cord 52 and the plug 54 may actually be connected to the apparatus 10.

In an alternative embodiment, a computer battery 120 may be embedded within the envelope of the apparatus 10, and included in the space near the fan 50 of the drive system 14 within the housing 12. A rating plate 110 or instruction plate 110 may provide the similar warnings, instructions, and connection details as discussed above.

Figure 16:
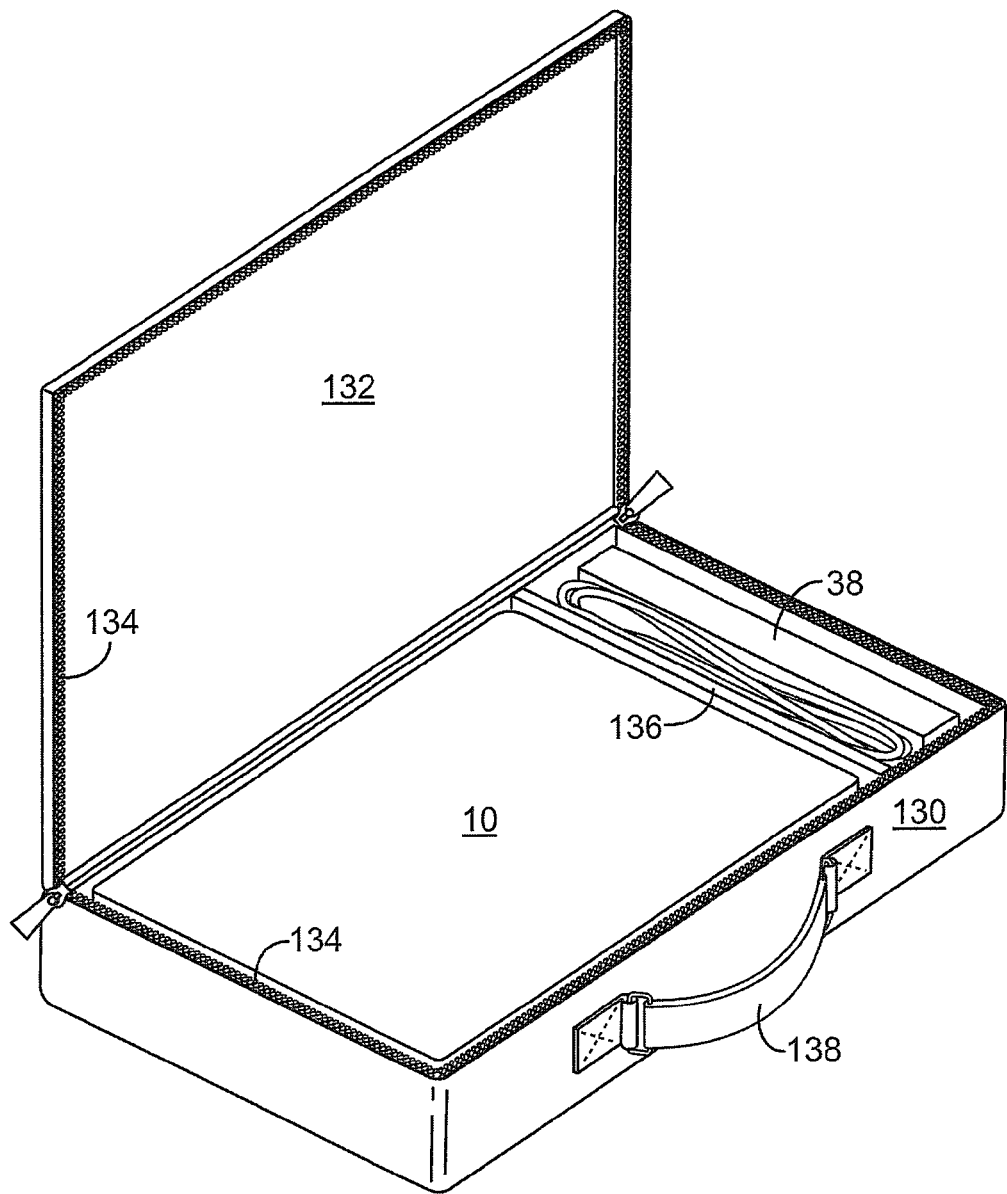
FIG. 16 is a perspective view of one embodiment of a carrying case suitable for packing an apparatus in accordance with the invention.

Referring to FIG. 16, a case 130 for an apparatus 10 may include a region for holding the apparatus 10, divided into compartments 137. For example, a compartment 137a may hold the apparatus 10, while a compartment 137b may hold a power supply 38, a folded cord 104, and the like. A closure 132, or lid 132 may be secured to the case 130 by a zipper 134 or other suitable mechanism.

Typically, a handle 136 for carrying may be adapted to a hand of a user, a shoulder strap, or the like. In the illustrated embodiment, the case 130 may be a conventional case, borrowed from the laptop computer market, may be or a specially designed case adapted to the apparatus 10. For example, the divider 136 may be moveable, and thus may be positionable within the case 130 in order to securely stow the apparatus 10, and still accommodate the power supply 38, cord 136, or other accoutrements associated with the apparatus 10.

In certain embodiments, the cord 104 may actually be wrapped around a spooling mechanism before the tubing 42. Likewise, the power supply 38 may be replaced with a battery 120 actually embedded in the apparatus 10. Thus, not all embodiments of an apparatus in accordance with the invention will require separate storage for a power supply 38 and cord 104.

Figure 17:
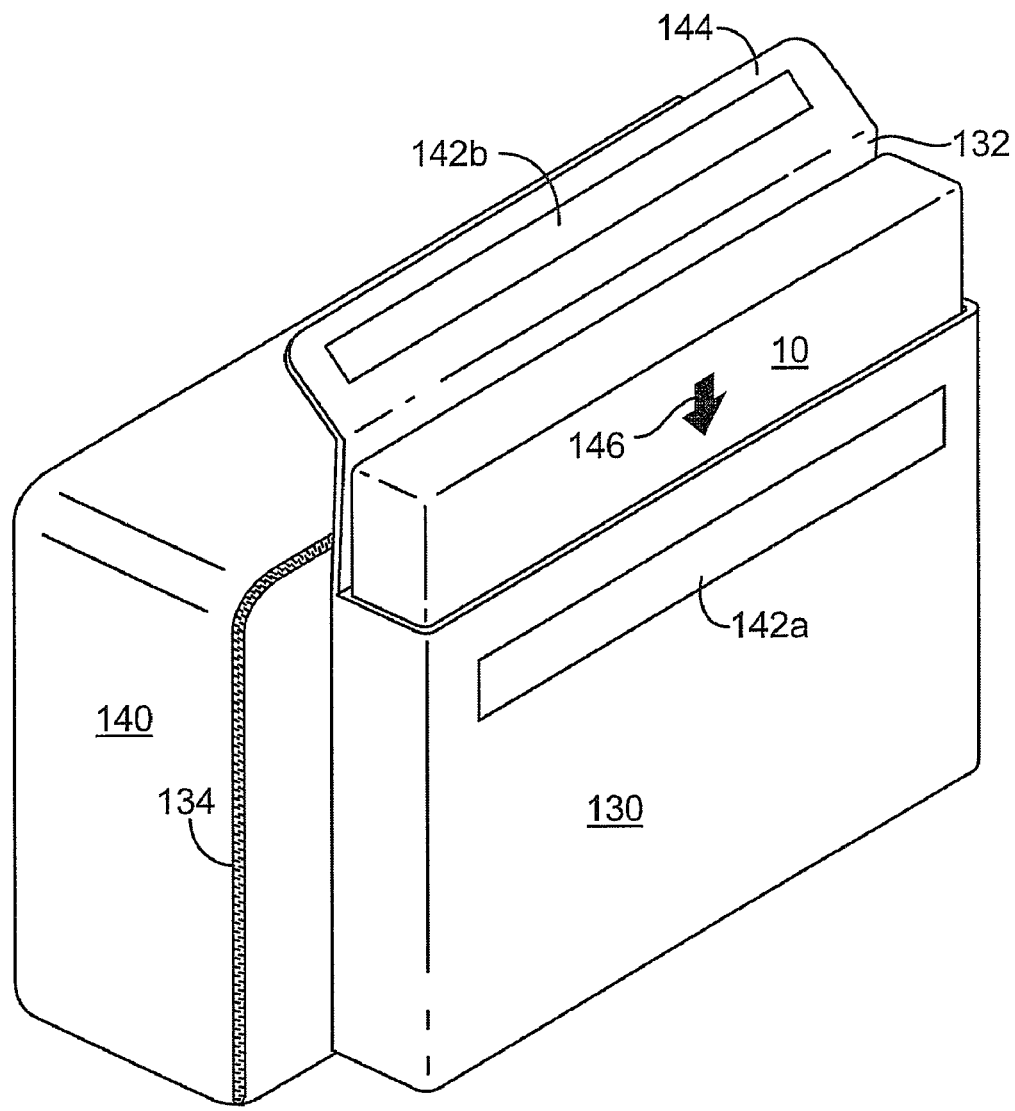
FIG. 17 is a perspective view of an alternative embodiment of a luggage system accommodating an apparatus in accordance with the invention.

Referring to FIG. 17, a case 130 suitable for holding the apparatus 10 may be a simple compartment 130 associated with other luggage 140, such as a briefcase. For example, certain suitcases, briefcases, and the like may be configured as a separate piece of luggage 140 having a pocket 130 interior or exterior thereto for receiving a laptop computer or the like. Accordingly, an apparatus 10 in accordance with the invention may be placed within the compartment 130 and closed by an appropriate lid 132 or cover 132 sealed by any appropriate mechanism.

In the illustrated embodiment, hook-and-loop fasteners may be formed as a securement mechanism 142 on the flap 144 and the outer portion of the case 130 or compartment 130 in order to form a proper securement keeping the lid 132 closed on the apparatus 10. Zipper closures 134 may be formed as appropriate in any particular location, including as the sealing mechanism for the lid 132 of the compartment 130. Any suitable system of handles, shoulder straps, and the like may be associated with the luggage 140 as known in the art.

Figure 18:
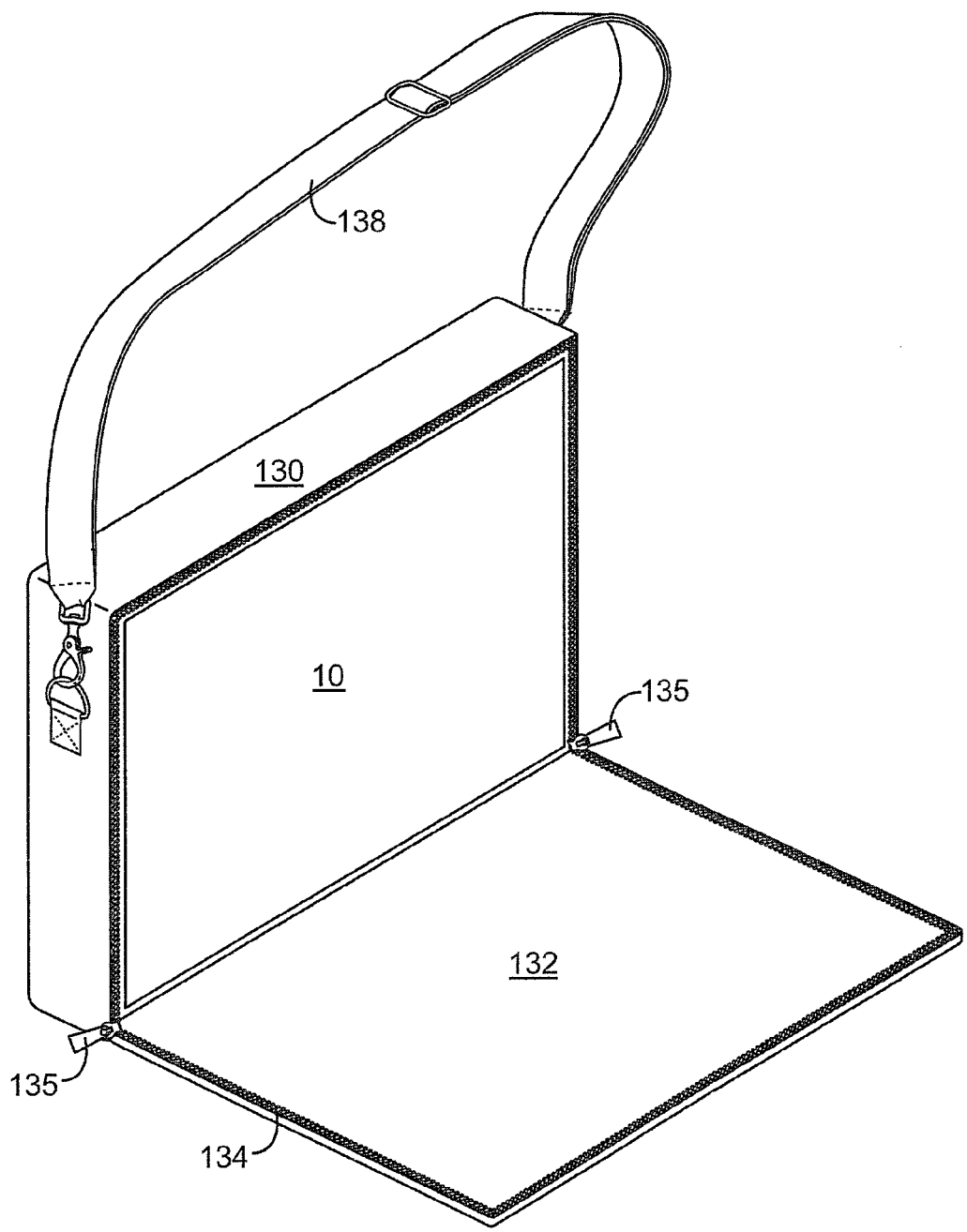
FIG. 18 is a perspective view of yet another alternative embodiment of a carrying case suitable for packing an apparatus in accordance with the invention.

Referring to FIG. 18, one embodiment of an apparatus 10 in accordance with the invention may be fitted into a case 130 having a closure 132 sealed by a zipper 134, or the like. Typically, a zipper pull 135 or more than one, may secure the zipper 134 to itself in order to close the cover 132 over the apparatus 10. Similarly, a variety of carrying straps 138 or handles 136 may be secured on various sides in order to promote convenient carrying. Meanwhile, the apparatus 10 may be fitted within the case 130 to be easily stowed, opened, inspected, and otherwise travel just as a laptop computer would.

In certain embodiments, the tubing 42 may be configured to fit on a reel. The reel may be operated by a crank in order to wind up the tubing 42 into the housing 12. In an alternative embodiment, the tubing 42 may be of a length selected to exactly fit with a single wrap or a few wraps about a spooling center portion 62. The shape of a laptop computer may actually contain four or five feet of hose along its periphery. Accordingly, in one method and apparatus in accordance with the invention, the system 10 may include a simple clip system around the outer periphery of the CPAP apparatus 10 suitable for holding the tubing 42 therearound.

In yet another embodiment, a computer battery may be fitted to the apparatus 10 in accordance with the invention. The power conditioning or the motor 50 may be sized to match the battery of an individual's laptop computer. Alternatively, a power supply, such as a battery of generic configuration having power conditioning for current, voltage, and the like may be adapted to power a laptop computer, the apparatus 10, or both. Thus, a computer battery may be matched to a user's apparatus 10, or vice versa.

In yet another alternative embodiment, the housing 12 may be configured as a "clam shell" configuration, having a hinge 42 at the back of two substantially identical halves. The drive system 14 may be configured near the center of the housing 12, with the delivery system 16, principally the hose 42 or tubing 42 wrapped therearound.

The present invention may be embodied in other specific forms without departing from its basic operational principles or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

I claim:

1. A CPAP apparatus comprising:
 a housing comprising top and bottom surfaces and having exterior, orthogonal dimensions of length, width, and height corresponding to those of a laptop computer;
 a drive system comprising a fan and a motor, the drive system connected to the housing and contained within the exterior dimensions;
 a flexible conduit having an outer diameter, a first end fitted to connect to the drive system, and a second end fitted to connect to a user interface to deliver CPAP therapy air from the fan and conduit into a breathing passage of a user;
 the housing, wherein a portion of each of the top and bottom surfaces defines a top and bottom flange, respectively, bounding an interior spacing separating the top and bottom flanges, a distance spanned by the interior spacing substantially matching the outer diameter of the flexible conduit, and
 the flexible conduit contained within the interior spacing and exterior dimensions.

2. The apparatus of claim 1, wherein the flexible conduit encircles at least a portion of the housing.

3. The apparatus of claim 1, wherein the top and bottom surfaces are substantially planar.

4. The apparatus of claim 1, wherein the top and bottom surfaces are substantially rectangular and sized to fit within the space allocated to a laptop computer in luggage configured to hold a laptop computer.

5. The apparatus of claim 1, further comprising a user interface configured to connect the second end of the flexible conduit to the breathing passage of the user.

6. The apparatus of claim 5, wherein the user interface is stowed within the exterior dimensions.

7. The apparatus of claim 1, wherein the top flange pivots with respect to the bottom flange.

8. The apparatus of claim 1, wherein the top flange comprises a console layer and a cover layer.

9. The apparatus of claim 8, wherein the cover layer pivots with respect to the console layer.

10. The apparatus of claim 9, wherein the console layer comprises a control panel receiving from a user input commands controlling operation of the drive system to deliver air to a human user at a controlled pressure selected for breathing by the user.

11. A CPAP apparatus comprising:
 a housing comprising top and bottom surfaces and having exterior, orthogonal dimensions of length, width, and height corresponding to those of a laptop computer;
 the housing, wherein a portion of each of the top and bottom surfaces defines a top and bottom flange, respectively, bounding an interior spacing separating the top and bottom flanges;
 a drive system comprising a fan and a motor sized and controlled to deliver CPAP therapy air to a user at a pressure and volume flow rate corresponding to breathing, the drive system connected to the housing and contained within the exterior dimensions; and
 a flexible conduit contained within the interior spacing and exterior dimensions and encircling the drive system, wherein a distance spanned by the interior spacing substantially matches an outer exterior diameter of the flexible conduit.

12. The apparatus of claim 11, wherein the top and bottom surfaces are substantially planar.

13. The apparatus of claim 11, wherein the top and bottom surfaces are substantially rectangular and sized to fit within the space allocated to a laptop computer in luggage configured to hold a laptop computer.

14. The apparatus of claim 11, further comprising a user interface configured to connect one end of the flexible conduit to at least one airway of a user.

15. The apparatus of claim 14, wherein the user interface is stowed within the exterior dimensions.

16. The apparatus of claim 11, wherein the top flange comprises a control interface receiving from a user input commands controlling operation of the drive system effective to control the CPAP therapy air delivered therefrom in at least one of pressure and volume flow rate at a value for breathing.

* * * * *